(12) United States Patent
Hu

(10) Patent No.: US 10,532,138 B2
(45) Date of Patent: *Jan. 14, 2020

(54) BREAST PUMP COMPRISING HEATING CUP

(71) Applicant: Lactans Healthcare Inc., Ningbo, Zhejiang (CN)

(72) Inventor: Min Hu, Ningbo (CN)

(73) Assignee: LACTANS HEALTHCARE INC., Ningbo (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,300

(22) Filed: Jun. 29, 2017

(65) Prior Publication Data

US 2017/0312410 A1 Nov. 2, 2017

Related U.S. Application Data

(63) Continuation of application No. 14/621,362, filed on Feb. 12, 2015, now Pat. No. 9,731,054.

(51) Int. Cl.
*A61M 1/06* (2006.01)
*A61F 7/00* (2006.01)

(52) U.S. Cl.
CPC ............. *A61M 1/062* (2014.02); *A61F 7/007* (2013.01); *A61M 1/064* (2014.02); *A61F 2007/0021* (2013.01); *A61F 2007/0088* (2013.01); *A61M 2205/3633* (2013.01); *A61M 2205/3653* (2013.01); *A61M 2205/8206* (2013.01)

(58) Field of Classification Search
CPC .................. A61M 1/062; A61M 1/064; A61M 2205/3633; A61M 2205/8206; A61M 2205/3653; A61F 7/007; A61F 2007/0088; A61F 2007/0021
See application file for complete search history.

(56) References Cited

U.S. PATENT DOCUMENTS

| | | | | |
|---|---|---|---|---|
| 4,573,969 | A * | 3/1986 | Schlensog | A61M 1/06 604/231 |
| 9,731,054 | B2 * | 8/2017 | Hu | A61F 7/007 |
| 2008/0262419 | A1 * | 10/2008 | Rollin | A61M 1/062 604/74 |
| 2008/0312586 | A1 * | 12/2008 | Thommen | A61M 1/064 604/74 |

* cited by examiner

*Primary Examiner* — Amber R Stiles
(74) *Attorney, Agent, or Firm* — David and Raymond Patent Firm

(57) ABSTRACT

A breast pump including a container, a host unit disposed above and communicating with the container, an electric heating cup disposed at the front end of the host unit and communicating with the container, an electric heating element, and heat insulation. The electric heating cup includes an inner cover and an outer cover which are integrated. The electric heating element and the heat insulation are disposed between the inner cover and the outer cover. The heat insulation is disposed between the electric heating element and the outer cover. Positive and negative electrodes of the electric heating element are connected to conducting plates disposed in the inner side of the outer cover via connection wires. The conducting plates extend to the outer side of the outer cover and are in electric connection to contact chips disposed at the lower front end of the host unit.

11 Claims, 6 Drawing Sheets

BREAST PUMP COMPRISING HEATING CUP

CROSS REFERENCE OF RELATED APPLICATION

This application is a Continuation application that claims the benefit of priority under 35 U.S.C. § 120 to a non-provisional application, application Ser. No. 14/621,362, filed Feb. 12, 2015, which are incorporated herewith by references in their entities.

BACKGROUND OF THE PRESENT INVENTION

Field of Invention

The invention relates to a breast pump comprising an electric heating cup.

Description of Related Arts

A typical breast pump employs carbon fiber, which is disposed outside the bell mouth thereof, as a heating element. The temperature of the heating element is controlled by an external temperature sensor. Thus, the breast pump has a complex structure and manufacturing process. In addition, the heating element is subject to the natural properties of the carbon fiber, which often has disadvantages such as non-uniform hot spots, irregular resistance variation, and the occurrence of focal temperature. Furthermore, conventional breast pumps are difficult to clean and sterilize thoroughly, as the abundant particles of fat and protein of the aerosolized milk tends to precipitate and accumulate in the inner walls of air path including pipes and diaphragms and gas drums of the pumps, which go bad in hours and bacteria thrives to be a source of pollution to the fresh milk in the container and a health risk to the mother's breasts.

SUMMARY OF THE PRESENT INVENTION

In view of the above-described problems, it is one objective of the invention to provide a breast pump that has a stable and compact structure, features a constant and safe heat supply, and is convenient to clean and sterilize.

To achieve the above objective, in accordance with one embodiment of the invention, there is provided a breast pump comprising a container, a host unit disposed above and communicating with the container, an electric heating cup disposed at a front end of the host unit and communicating with the container, an electric heating element, and heat insulation. The electric heating cup comprises an inner cover and an outer cover which are integrated; the electric heating element and the heat insulation are disposed between the inner cover and the outer cover; the heat insulation is disposed between the electric heating element and the outer cover; positive and negative electrodes of the electric heating element are connected to conducting plates disposed in an inner side of the outer cover via connection wires, respectively; the conducting plates extend to an outer side of the outer cover and are in electric connection to contact chips disposed at a lower front end of the host unit.

In a class of this embodiment, the breast pump further comprises a connecting piece. The connecting piece is disposed above the container and a lower end thereof is in seal connection to the container; a conduit protrudes from a front end of the connecting piece and is in fixed seal connection to the electric heating cup; the connecting piece comprises a through hole; the host unit is fixed on the connecting piece and comprises a suction pipe; the suction pipe is inserted into the through hole and the connecting piece is in seal connection to the container.

In a class of this embodiment, the host unit comprises a miniature diaphragm vacuum pump, a miniature magnetic valve, and an air loop comprising an air inlet and an air outlet; an air inlet of the miniature diaphragm vacuum pump and an air outlet of the miniature magnetic valve communicate with each other and both are connected to the air inlet of the air loop; an air inlet of the magnetic valve and an air outlet of the miniature diaphragm vacuum pump are both connected to the air outlet of the air loop.

In a class of this embodiment, the air inlet of the air loop is a suction pipe.

In a class of this embodiment, the electric heating element is an electric heating film, which is fixed on one side of the inner cover facing the outer cover; the heat insulation is fixedly attached to one side of the electric heating film facing the outer cover; one end of the conducting plates is disposed between the inner cover and the outer cover, and is connected to the electric heating film via connection wires; and the other end of the conducting plates is exposed out of the outer cover. Still further objects and advantages will become apparent from a consideration of the ensuing description and drawings.

In a class of this embodiment, the electric heating film comprises a plurality of sheets affixed at intervals on the side of the inner cover facing the outer cover, and the sheets are connected in parallel with one another and connected to the conducting plates.

In a class of this embodiment, the inner cover and the outer cover are both made of food-grade hard plastic material free of bisphenol amine.

In a class of this embodiment, the electric heating film is made of polytetrafluoroethylene-based temperature-constant far infrared electric heating material.

In a class of this embodiment, the conducting plates and the contact chips are gold-plated copper sheets.

In a class of this embodiment, two face-to-face walls of the inner cover and the outer cover comprise a plurality of reinforcing ribs matching with one another; the reinforcing ribs of the inner cover comprises a plurality of ultrasonic welding protrusions; the reinforcing ribs of the outer cover comprises a groove, which corresponds to the ultrasonic welding protrusions of the inner cover; the inner cover comprises a cylindrical protrusion at a center thereof, and the cylindrical protrusion comprises at least one groove for mounting an O-shaped silicone seal ring and an ultrasonic welding collar comprising a plurality of gaps.

The breast pump comprises the electric heating cup comprising the inner cover and the outer cover, and the electric heating element clamped between the inner cover and the outer cover, all of which are fabricated into an integrated structure by secondary injection molding, ultrasonic welding technology, and lathe grinding and polishing processing. The electric heating element is fixed between the inner cover and the outer cover, so it is not easy to detach, convenient for cleaning, and has impact and beautiful appearance. The conducting plates of the electric heating cup are fixed on the outer cover through secondary injection molding and are in electric connection to the contact chips at the lower front end of the host unit. Thus, the structure is simple, compact, stable and convenient for use and mass production. The resulting electric heating cup is made of opaque material, so the users cannot see the electric heating element and connection wires, providing the users with the sense of safety. Lathe grinding and polishing processing make the edge of the cup, where the inner cover and outer cover ultrasonic welded together, looks like one integrated and seamless part without any joint line visible, providing the users with the sense of hygiene.

In addition, the reinforcing ribs disposed on the inner walls of both inner cover and outer cover of the electric heating cup, ultrasonic welding protrusions, grooves, O-shaped silicone seal ring, and gaps on the cylindrical protrusion of the inner cover, on one hand, cooperate with each other to enable the inner cover and the outer cover to be connected firmly whereby forming an integrated structure, on the other hand, the resulting structure is sealed and waterproof in boiling water. In the process of boiling the electric heating cup for sterilization, air between the inner cover and the outer cover tends to inflate, thereby deforming the O-shaped silicone ring, so that the heated air breaks through the sealing of the O-shaped silicone ring and is released through the gaps. Thus, the space between the inner cover and the outer cover is approximately in the vacuum state under high temperatures, thereby preventing the electric heating cup from deforming or broken. When the heated air with high pressure releases through the gaps, air bubbles emerging in the boiling water, water is prevented to get inside of the electric heating cup. Thus, high-grade waterproof achieves, so long as the cup is taken out of the water when it is still boiling, for cooling water may be siphoned inside to the cup.

The host unit comprises a miniature diaphragm vacuum pump, a miniature magnetic valve, and an air loop comprising an air inlet and an air outlet. The suction pipe of the host unit mentioned above also acts as the air inlet of the air loop. An air inlet of the miniature diaphragm vacuum pump and an air outlet of the miniature magnetic valve communicate with each other and both are connected to the air inlet of the air loop; an air inlet of the magnetic valve and an air outlet of the miniature diaphragm vacuum pump are both connected to the air outlet of the air loop. To clean the breast pump, the air inlet of the air loop and the air outlet of the air loop each are connected to straws. The straw of the air inlet is inserted into a container containing medical alcohol, and the straw of the air outlet is inserted into a hollow container. Start the breast pump in the cleaning mode, the medical alcohol fluid is siphoned to every space of the air loop under the drive of the vacuum pump, whereby completely disinfecting the breast pump, each cleaning lasts for only about 10 seconds, and finally the effluent is collected by the hollow container. On this occasion, the vacuum pump acts as a water pump temporarily. After that, move the air inlet away from the medical alcohol and remain the breast pump working for a while, the alcohol residue evaporates quickly and the air loop and the diaphragm vacuum pump remain dry to protect the mechanical properties of the diaphragm vacuum pump and insure the service life of the breast pump.

These and other objectives, features, and advantages of the present invention will become apparent from the following detailed description, the accompanying drawings, and the appended claims.

DETAILED DESCRIPTION OF THE PREFERRED EMBODIMENT

Figure 1:
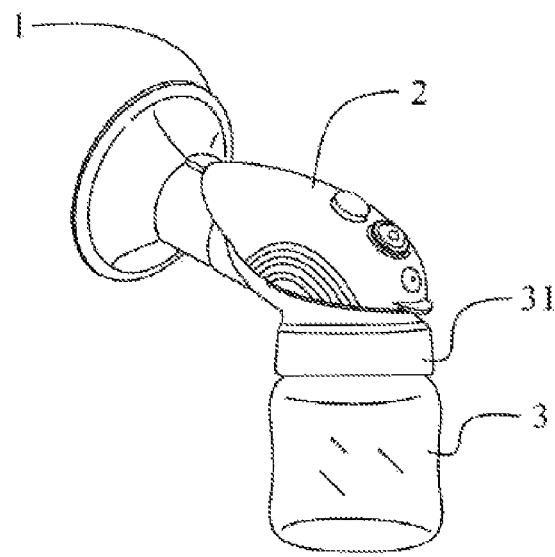
FIG. 1 is a stereogram of a breast pump in accordance with one embodiment of the invention.
Figure 2:
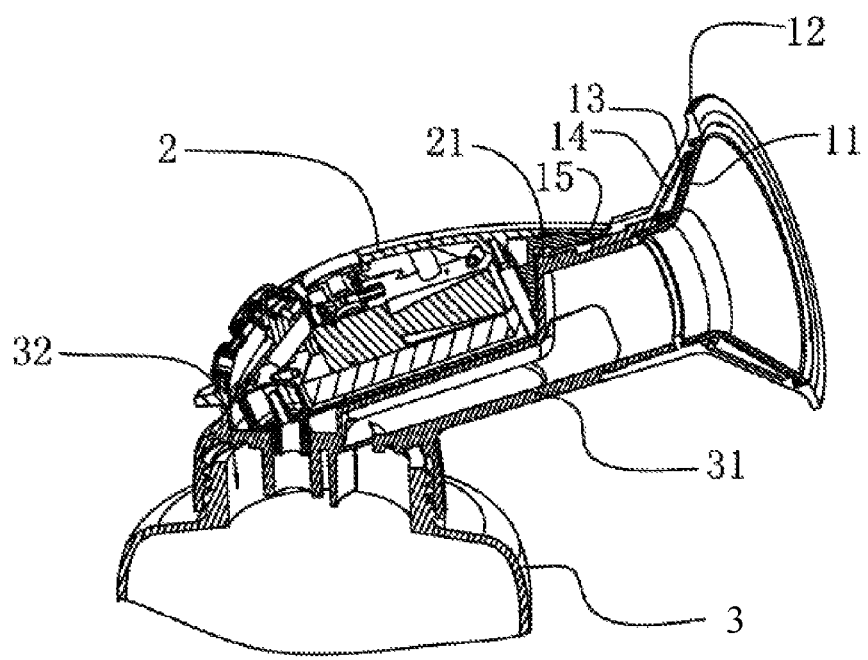
FIG. 2 is a local sectional view of a breast pump in accordance with one embodiment of the invention.

For further illustrating the invention, experiments detailing of a breast pump are described below. It should be noted that the following examples are intended to describe and not to limit the invention.

As shown in FIGS. 1-6, a breast pump of the invention comprises a container 3, a host unit 2 disposed above and communicating with the container, an electric heating cup 1 disposed at the front end of the host unit 2 and communicating with the container 3. The host unit 2 comprises a miniature diaphragm vacuum pump, a miniature magnetic valve configured to generate vacuum negative pressure, an air loop comprising an air inlet and an air outlet, an integrated circuit board, and a rechargeable lithium polymer battery for supply power for the breast pump. The front end of the electric heating cup 1 is in the shape of a horn, and its diameter is slightly larger than that of a mother's areola, so that the electric heating cup 1 better contacts the areola. The rear end of the electric heating cup 1 has an inner diameter larger than that of a mother's nipple, which, preferably, is twice the outer diameter of the nipple, forming a "nipple tunnel". The rear end of the electric heating cup 1 is a straight pipe with a round cross section and has certain length thereby ensuring enough space for nipple and protecting the nipple from squeezing.

Preferably, the breast pump comprises a connecting piece 3 at the top thereof. The connecting piece 31 is disposed above the container 3 and the lower end thereof is in seal connection to the container 3 by thread screw. A silicone flat washer 34 is disposed between the connecting piece and the container 3. A conduit protrudes from a front end of the connecting piece 31 and is in fixed seal connection to the rear end of the electric heating cup 1. The opening of the conduit is a straight pipe with a round cross section, on which at least one O-shaped silicone seal ring 33 is disposed. The connecting piece 31 comprises a through hole 32. The host unit 2 is fixed on the connecting piece 31 and comprises a suction pipe 22. The suction pipe 22 is also disposed with an O-shaped silicone seal ring. The suction pipe 22 is inserted into the through hole 32 and is in seal connection to the connecting piece 31, while the connecting piece 31 is in seal connection to the container 3. The front end of the connecting piece 31 is connected to the rear end of the electric heating cup 1 via plugging, screw thread, or bayonet screwing.

Figure 3:
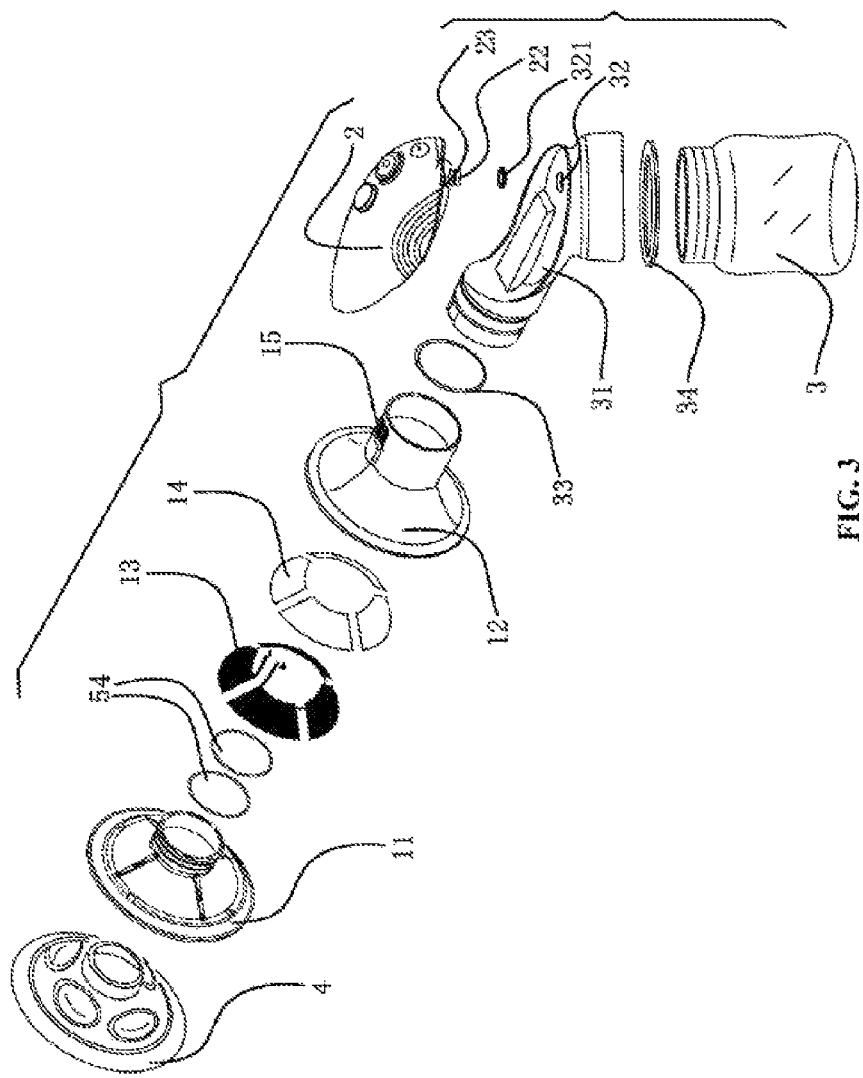
FIG. 3 is a local exploded view of a breast pump in accordance with one embodiment of the invention.
Figure 4:
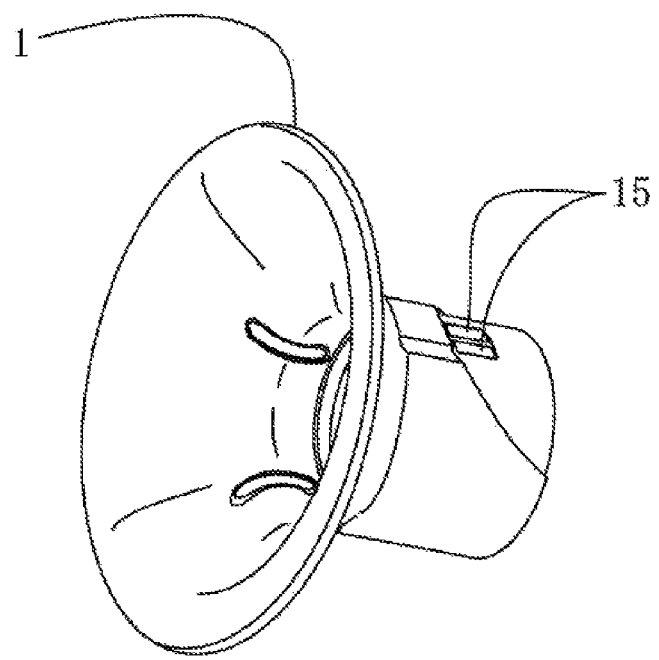
FIG. 4 is a stereogram of an electric heating cup of a breast pump in accordance with one embodiment of the invention.
Figure 5:
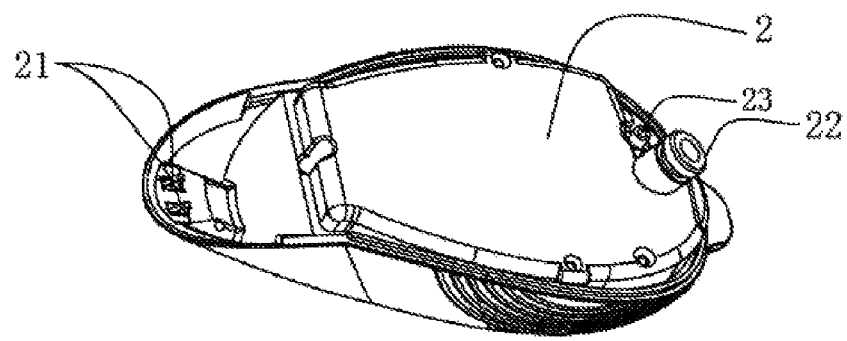
FIG. 5 is a stereogram of a host unit of a breast pump in accordance with one embodiment of the invention.
Figure 6:
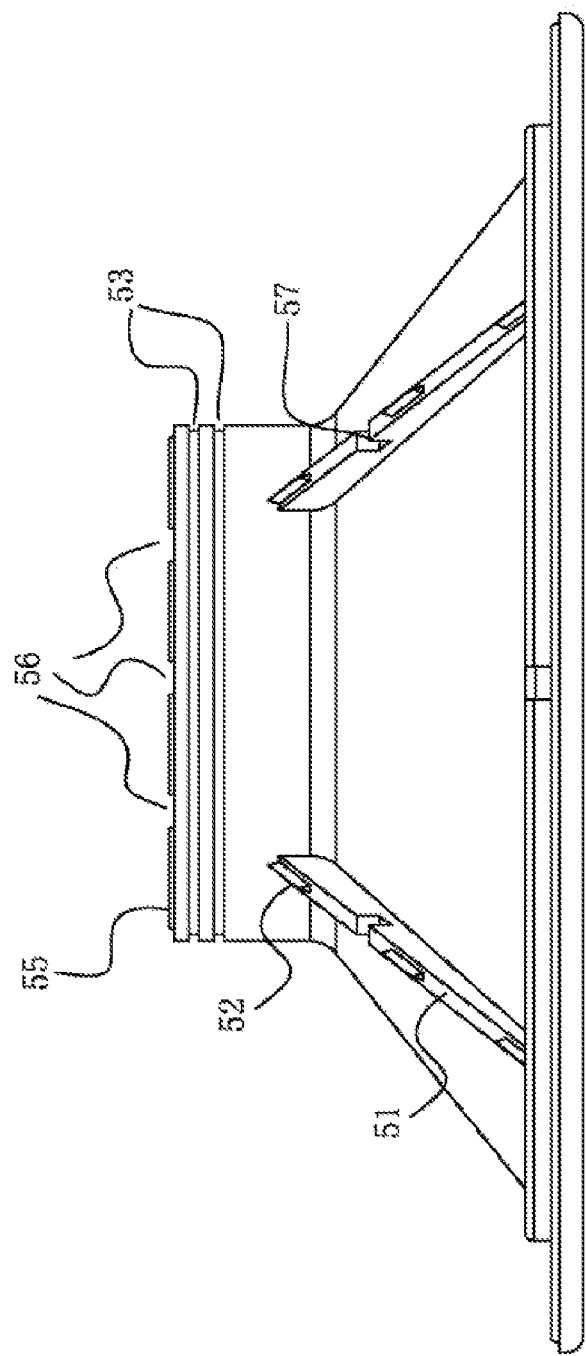
FIG. 6 is a schematic diagram of an inner cover of a breast pump in accordance with one embodiment of the invention.
Figure 7:
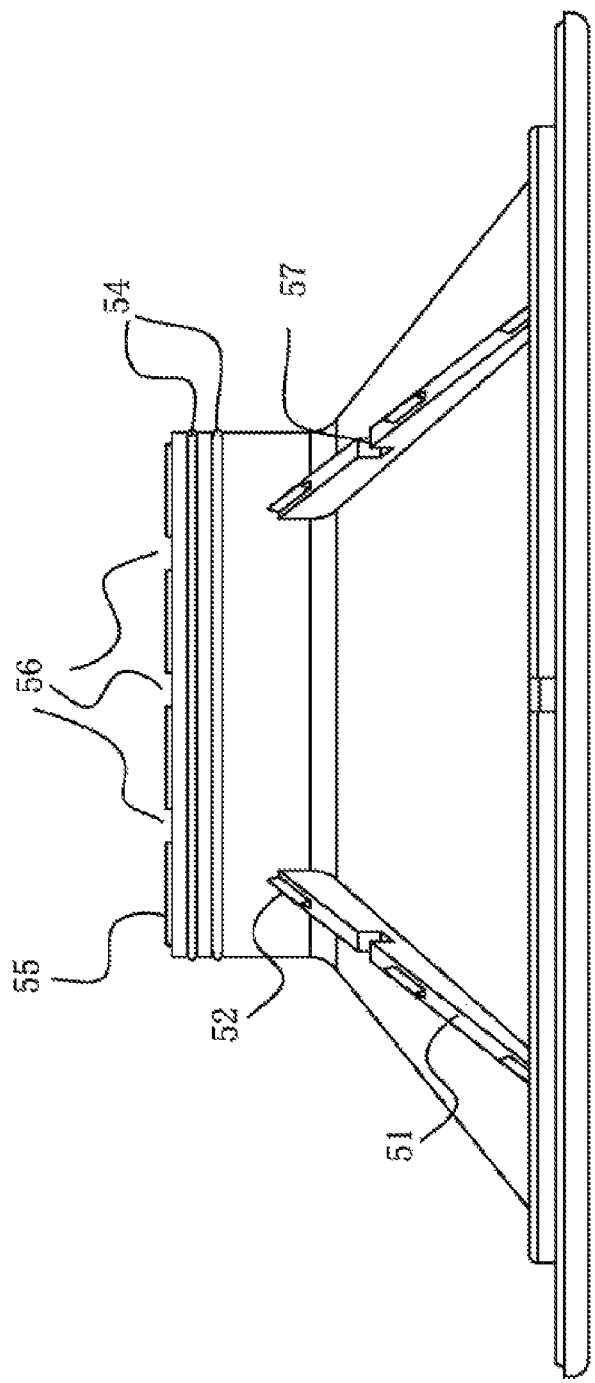
FIG. 7 is a schematic diagram of an inner cover of a breast pump equipped with at least one O-shaped silicone seal ring in accordance with one embodiment of the invention.
Figure 8:
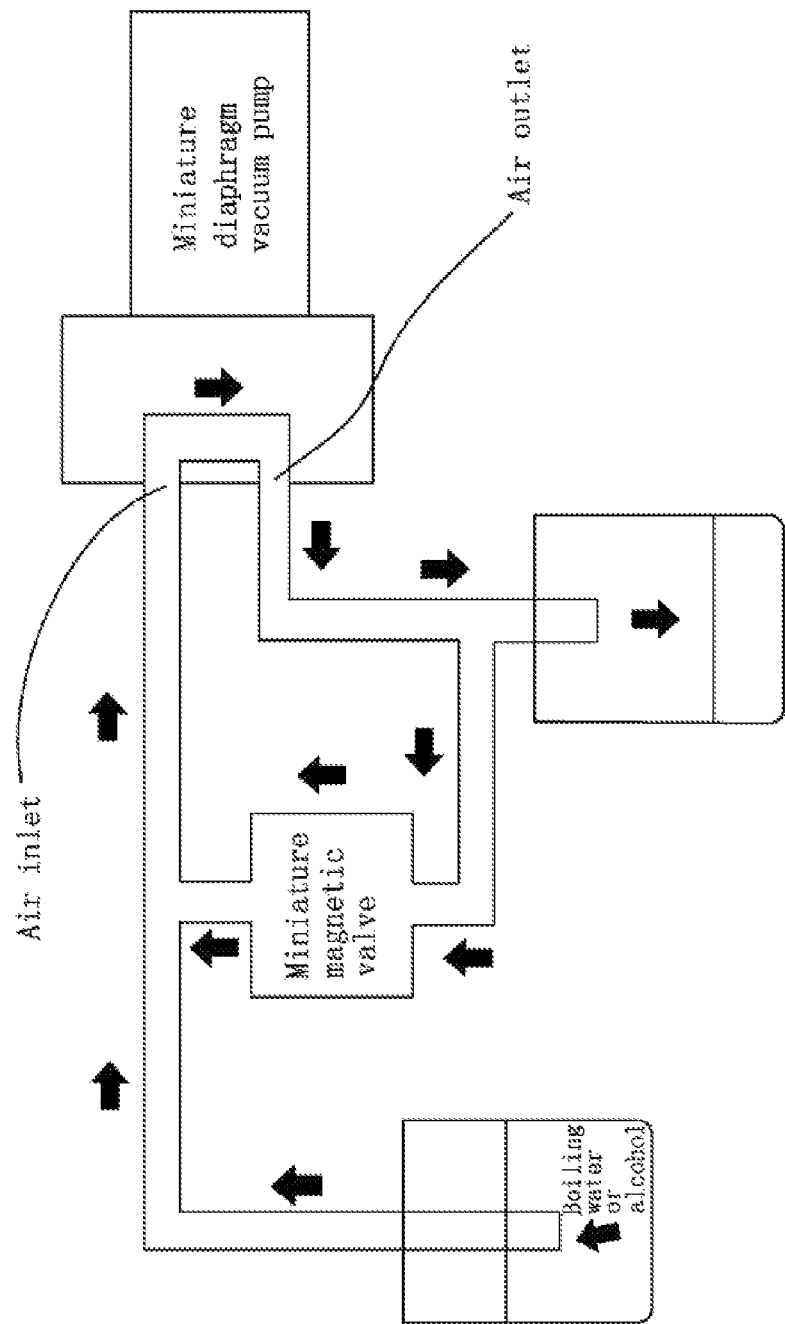
FIG. 8 is a work flow chart for cleaning an air loop of a breast pump in accordance with one embodiment of the invention.

The electric heating cup 1 comprises an inner cover 11 and an outer cover 12, as shown in FIG. 3. The electric heating element and the heat insulation 14 are disposed between the inner cover 11 and the outer cover 12. The electric heating element is an electric heating film, electric heating wire, or other electric heating materials. Preferably, the electric heating element is an electric heating film 13, which is fixed on one side of the inner cover 11 facing the outer cover 12; the heat insulation 14 is fixedly attached to one side of the electric heating film 13 facing the outer cover 12. The heat insulation 14 is disposed between the electric heating element and the outer cover 12; positive and negative electrodes of the electric heating element are connected to conducting plates 15 disposed in an inner side of the outer cover 12 via connection wires, respectively; the conducting plates 15 extend to an outer side of the outer cover 12 and are in electric connection to contact chips 21 disposed at a lower front end of the host unit 2. Preferably, one end of the conducting plates 15 is disposed between the inner cover 11 and the outer cover 12, and is connected to the electric heating film 13 via connection wires; and the other end of the conducting plates 15 is exposed out of the outer cover 12.

When the electric heating cup 1 is connected to the front end of the connecting piece 31, the host unit 2 is clasped on the connecting piece 31, so that the contact chips 21 disposed at the lower front end of the host unit 2 well contact the conducting plates 15. Thus, the power source of the host unit supplies power for the electric heating cup 1 via the contact chips 21 and the conducting plates 15.

The inner cover 11 and the outer cover 12 and the connecting piece are all made of food grade hard plastic material free of bisphenol amine, for example, polypropylene (PP), preferably, TRITAN copolymer from Eastman Chemical Company of U.S.A Optionally, thermoplastic engineering plastic with high temperature resistance of exceeding 207° C., such as polyphenylene sulfone resin (PPSU), is also practicable.

The host unit comprises a miniature diaphragm vacuum pump, a miniature magnetic valve, and an air loop comprising an air inlet and an air outlet 23. The suction pipe 22 of the host unit mentioned above also acts as the air inlet of the air loop. An air inlet of the miniature diaphragm vacuum pump and an air outlet 23 of the miniature magnetic valve communicate with each other and both are connected to the air inlet of the air loop; an air inlet of the magnetic valve and an air outlet of the miniature diaphragm vacuum pump are both connected to the air outlet 23 of the air loop. To clean the breast pump, the air inlet of the air loop and the air outlet of the air loop each are connected to straws. The straw of the air inlet is inserted into a container containing medical alcohol, and the straw of the air outlet is inserted into a hollow container. The breast pump is disposed with an integrated circuit board with a controller IC. A control program is made to provide several different modes of sucking by regulating the scale of working time of the miniature magnetic valve while the miniature diaphragm vacuum pump works all the time. The cleaning mode is set to open the miniature magnetic valve when the vacuum pump keeps working. Start the breast pump in the cleaning mode, the medical alcohol fluid is siphoned to every space of the air loop under the drive of the vacuum pump, whereby completely disinfecting the breast pump, each cleaning lasts for about 10 seconds, and finally the effluent is collected by the hollow container. On this occasion, the vacuum pump acts as a water pump temporarily. After that, move the air inlet away from the medical alcohol and remain the breast pump working for a while, the alcohol residue evaporates quickly and the air loop and the diaphragm vacuum pump remain dry to protect the mechanical properties of the diaphragm vacuum pump and insure the service life of the breast pump.

Upon manufacturing the electric heating cup 1, the outer cover 12 is prepared using the secondary injection molding technology. First, two conducting plates 15 are molded by injection together to form an insert, which is further molded by injection with the outer cover 12, so that the conducting plates 15 and the outer cover 12 are integrated. Specifically, one end of the conducting plates 15 is disposed at the inner side of the outer cover 12, and the other end of the conducting plates 15 is exposed out of the outer cover 12. The exposed part of the conducting plates 15 is in seamless connection to the outer side of the outer cover 12, and both are in the same plane without height difference. Thereafter, the electric heating film 13 and the heat insulation 14 are fixed on one side of the inner cover 11 facing the outer cover 12, and the positive and negative electrodes of the electric heating film 13 are connected to the conducting plates with connecting wires, respectively. In the presence of ultrasonic wave, the inner cover 11 and the outer cover 12 of the electric heating cup 1 are welded and sealed to form an integrated structure. Look from the outside cover, no connection wires and socket connectors can be observed. Only two conducting plates 15 disposed in parallel on the outer side of the outer cover 12 can be observed. That the contact chips 21 disposed at the lower front end of the host unit 2 are connected to the conducting plates 15 on the outer cover 12 by contact makes the breast bump have a simple structure, convenient power supply and beautiful appearance.

Preferably, the electric heating film 13 is made of polytetrafluoroethylene-based temperature-constant far infrared electric heating material, has a working voltage of 7.4 V DC and a thickness of 0.2-0.5 mm. The electric heating film 13 comprises a plurality of sheets affixed at intervals, between the reinforcing ribs, on the side of the inner cover 11 facing the outer cover 12. Preferably, the electric heating film 13 employs 4 sheets having a size of 15 mm×30 mm. The sheets are connected in parallel with one another via conductive copper foils and wires. The conductive copper foils are fixed on each sheet through conductive adhesives, preferably. The sheets can be fixed on the inner wall of the inner cover 13 through conventional thin double-sided adhesive tape and are connected in parallel with one another with wires by soldering and connected to the conducting plates 15 by connecting wires by soldering as well. The heat insulation 14 is, preferably, flexible foam sheet with back adhesive and having a thickness of 2 or 3 mm, which can be firmly attached to the electric heating film 13, thereby preventing the detaching of the electric heating film from the inner cover, protecting the far infrared energy from emitting outside to the outer cover 12, so that the far infrared energy is concentrated to irradiate to the mother's areola, thereby ensuring good thermal therapy effect and saving electric energy.

The working voltage of the electric heating film 13 is 7.4 VDC, the resistance thereof is about 30 ohm, and the power thereof is about 1.8 W. Such low power enables the host unit to employ a miniature rechargeable lithium polymer battery, so that the breast pump is small and convenient for carrying and using. In addition, the working temperature of the electric heating cup is constantly at 38-42° C., which is the optimal temperature for the thermal therapy for a mother's areola, So, no matter in winter or summer, the use of the breast pump makes users feel warm and comfortable as if baby suckling. Mothers have used "wet heat" to the breasts to expand the tissue and ducts and start the flow of milk before pumping with conventional breast pumps, in the situation of breast engorgement. The far infrared energy from the electric heating cup thereof makes things much easier and better and perhaps acts as a signal to trigger milk production and release as well.

Optionally, a detachable silicone protection pad 4 is disposed at the inner side of the electric heating cup 1. The silicone protection pad 4 has adapted curve surface with the electric heating cup and comprises convex points for massage, thereby improving the usage comfort.

The breast pump comprises the electric heating cup comprising the inner cover and the outer cover, and the electric heating element clamped between the inner cover and the outer cover, all of which are fabricated into an integrated structure by secondary injection molding and ultrasonic welding technology. The electric heating element is fixed between the inner cover and the outer cover, so it is not easy to detach, convenient for cleaning and sterilizing, and has impact and beautiful appearance.

The conducting plates are fixed on the outer cover 12 through secondary injection molding and are in electric connection to the contact chips at the lower front end of the host unit. Thus, the structure is simple, compact, stable and convenient for use and mass production. The resulting electric heating cup is made of opaque material, so the users cannot see the electric heating element and connection wires, providing the users with the sense of safety.

Preferably, the conducting plates 15 and the contact chips 21 are a gold-plated copper sheet. The gold-plated copper sheet has excellent electrical conductivity, and looks shining, easy to clean and difficult to rust, which ensures the beautiful appearance of the product.

In addition, two face-to-face walls of the inner cover and the outer cover comprise a plurality of reinforcing ribs 51 matching with one another; the reinforcing ribs of the inner cover comprises a plurality of ultrasonic welding protrusions 52; the reinforcing ribs of the outer cover comprises grooves, which correspond to the ultrasonic welding protrusions of the inner cover; the inner cover comprises a cylindrical protrusion at a center thereof, and the cylindrical protrusion comprises at least one groove 53 for mounting an O-shaped silicone seal ring 54 and an ultrasonic welding collar 55 comprising a plurality of gaps 56. The reinforcing ribs 51 of the inner cover also comprise gaps 57 for allowing the conductive wires to pass through.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A heating cup for a breast pump, comprising:
   an inner cover;
   an outer cover;
   a heating element fixed between said inner cover and said outer cover;
   a plurality of conducting plates fixed on said outer cover, wherein said plurality of conducting plates conductively connects to said heating element, wherein through conducting from said conducting plate, said heating element generates heat; and
   a heat insulation, wherein said heat insulation is disposed between said heating element and said outer cover for concentrating a far infrared energy to irradiate an areola of a breast of a user.

2. The heating cup for a breast pump, as recited in claim 1, further comprising a protection pad detachably disposed at an inner side of said heating cup.

3. A heating cup for a breast pump, comprising:
   an inner cover;
   an outer cover;
   a heating element fixed between said inner cover and said outer cover, wherein said heating element is an electric heating film; and
   a plurality of conducting plates fixed on said outer cover, wherein said plurality of conducting plates conductively connects to said heating element, wherein through conducting from said conducting plate, said heating element generates heat.

4. The heating cup for a breast pump, as recited in claim 3, wherein said electric heating film comprises a plurality of sheets affixed on the side of said inner cover facing said outer cover, wherein said sheets are conductively connected to said conducting plates.

5. The heating cup for a breast pump, as recited in claim 4, wherein said inner cover further comprises a plurality of reinforcing ribs, wherein said sheets are affixed at an interval between said reinforcing ribs on the side of said inner cover facing said outer cover.

6. The heating cup for a breast pump, as recited in claim 5, wherein said outer cover further comprises a plurality of reinforcing ribs, wherein said reinforcing ribs of said inner cover further comprises a plurality of protrusions, wherein said reinforcing ribs of said outer cover further comprises a plurality of grooves, which correspond to the protrusions of said inner cover.

7. A breast pump, comprising:
   a heating cup which comprises an inner cover, an outer cover, a heating element fixed between said inner cover and said outer cover, a plurality of conducting plates fixed on said outer cover, and a heat insulation disposed between said heating element and said outer cover for concentrating a far infrared energy to irradiate an areola of a breast of a user, wherein said conducting plates are disposed on said outer cover, wherein said conducting plates conductively connect to said heating element;
   a host unit conductively connected with said heating cup for supplying energy to said heating cup, so that said heating cup is capable of heating;
   a container, wherein said container communicates with said heating cup and said host unit respectively; and
   a connecting piece, wherein said host unit fixes on and communicates with said connecting piece, wherein said connecting piece is disposed above and communicates with said container, wherein said heating cup is disposed in front of and communicates with said connecting piece.

8. A breast pump, comprising:
   a heating cup which comprises an inner cover, an outer cover, a heating element fixed between said inner cover and said outer cover, a plurality of conducting plates fixed on said outer cover, wherein said conducting plates are disposed on said outer cover, wherein said conducting plates conductively connect to said heating element, wherein said heating element is an electric heating film, wherein said electric heating film comprises a plurality of sheets affixed on a side of said inner cover facing said outer cover, wherein said sheets are conductively connected to said conducting plates;
   a host unit conductively connected with said heating cup for supplying energy to said heating cup, so that said heating cup is capable of heating;
   a container, wherein said container communicates with said heating cup and said host unit respectively;

a connecting piece, wherein said host unit fixes on and communicates with said connecting piece, wherein said connecting piece is disposed above and communicates with said container, wherein said heating cup is disposed in front of and communicates with said connecting piece.

9. The breast pump, as recited in claim 8, wherein said inner cover further comprises a plurality of reinforcing ribs, wherein said plurality of reinforcing ribs of said inner cover further comprises a plurality of protrusions, wherein said outer cover further comprises a plurality of reinforcing ribs, wherein said plurality of reinforcing ribs of said outer cover further comprises a plurality of grooves, which correspond to the protrusions of said inner cover.

10. A breast pump, comprising:
a heating cup which comprises an inner cover, an outer cover, a heating element fixed between said inner cover and said outer cover, a plurality of conducting plates fixed on said outer cover, wherein said conducting plates are disposed on said outer cover, wherein said conducting plates conductively connect to said heating element, wherein said heating element is an electric heating film, wherein said electric heating film comprises a plurality of sheets affixed on a side of said inner cover facing said outer cover, wherein said sheets are conductively connected to said conducting plates;
a host unit conductively connected with said heating cup for supplying energy to said heating cup, so that said heating cup is capable of heating, wherein said host unit comprises a controller and a power supplier, wherein said controller controls said power supplier to supply energy to said heating cup, so that when said heating cup is working, said heating cup heats to a constant working, wherein said host unit further comprises a vacuum pump, a magnetic valve and an air loop, wherein said air loop communicates with said vacuum pump, said magnetic valve and said connecting piece respectively;
a container, wherein said container communicates with said heating cup and said host unit respectively; and
a connecting piece, wherein said host unit fixes on and communicates with said connecting piece, wherein said connecting piece is disposed above and communicates with said container, wherein said heating cup is disposed in front of and communicates with said connecting piece.

11. The breast pump, as recited in claim 10, wherein said air loop further comprising an air inlet and an air outlet, an air inlet of said vacuum pump and an air outlet of said magnetic valve communicating with each other and both are connected to said air inlet of said air loop, an air inlet of said vacuum valve and an air outlet of said outlet of said vacuum pump are both connected to said air outlet of said air loop.

* * * * *